United States Patent
Rübben

(10) Patent No.: US 8,974,520 B2
(45) Date of Patent: Mar. 10, 2015

(54) METHOD FOR PRODUCING A BIOACTIVE SURFACE ON THE BALLOON OF A BALLOON CATHETER

(76) Inventor: Alexander Rübben, Monaco (MC)

( * ) Notice: Subject to any disclaimer, the term of this patent is extended or adjusted under 35 U.S.C. 154(b) by 843 days.

(21) Appl. No.: 13/055,143

(22) PCT Filed: Jul. 21, 2009

(86) PCT No.: PCT/EP2009/005568
§ 371 (c)(1),
(2), (4) Date: Apr. 21, 2011

(87) PCT Pub. No.: WO2010/009904
PCT Pub. Date: Jan. 28, 2010

(65) Prior Publication Data
US 2011/0190696 A1    Aug. 4, 2011

(30) Foreign Application Priority Data

Jul. 22, 2008  (DE) .......................... 10 2008 034 826

(51) Int. Cl.
*A61F 2/06*    (2013.01)
*A61L 29/16*    (2006.01)

(52) U.S. Cl.
CPC ........... *A61L 29/16* (2013.01); *A61L 2300/204* (2013.01); *A61L 2300/404* (2013.01); *A61L 2420/02* (2013.01)
USPC ............. 623/1.42; 29/428; 424/423; 427/2.1; 604/103.02; 604/509; 604/96.01; 606/192; 623/1.46

(58) Field of Classification Search
USPC .................... 14/1; 29/428; 424/423; 427/2.1; 604/103.02, 509, 96.01; 606/192; 623/1.46
See application file for complete search history.

(56) References Cited

U.S. PATENT DOCUMENTS

| | | | |
|---|---|---|---|
| 5,021,045 A * | 6/1991 | Buckberg et al. | 604/500 |
| 5,102,402 A | 4/1992 | Dror | |
| 5,331,027 A * | 7/1994 | Whitbourne | 524/37 |
| 5,707,385 A * | 1/1998 | Williams | 606/192 |
| 6,129,705 A | 10/2000 | Grantz | |
| 6,287,628 B1 | 9/2001 | Hossainy | |
| 6,306,166 B1 * | 10/2001 | Barry et al. | 623/1.46 |
| 6,369,039 B1 | 4/2002 | Palasis | |
| 7,601,382 B2 * | 10/2009 | Weber et al. | 427/2.1 |
| 2004/0044404 A1 * | 3/2004 | Stucke et al. | 623/1.46 |
| 2006/0030936 A1 * | 2/2006 | Weber et al. | 623/1.42 |
| 2007/0088255 A1 * | 4/2007 | Toner et al. | 604/96.01 |
| 2008/0118544 A1 * | 5/2008 | Wang | 424/423 |
| 2010/0015200 A1 * | 1/2010 | McClain et al. | 424/423 |
| 2010/0087783 A1 * | 4/2010 | Weber et al. | 604/103.02 |
| 2010/0179475 A1 * | 7/2010 | Hoffmann et al. | 604/103.02 |
| 2010/0298769 A1 * | 11/2010 | Schewe et al. | 604/96.01 |
| 2011/0054396 A1 * | 3/2011 | Kangas et al. | 604/103.02 |
| 2011/0067778 A1 * | 3/2011 | Mitchell et al. | 141/1 |

FOREIGN PATENT DOCUMENTS

WO    2008/008126 A1    1/2008
WO    2008061642 A2    5/2008

OTHER PUBLICATIONS

"What is an Azeotrope?" Bright Hub Engineering, 2012. Accessed Aug. 30, 2013 online: <http://www.brighthubengineering.com/manufacturing-technology/112074-what-is-an-azeotrope/>.*

* cited by examiner

*Primary Examiner* — Scott Medway
(74) *Attorney, Agent, or Firm* — Gudrun E. Huckett

(57) ABSTRACT

The invention relates to a method for producing a bioactive surface on the balloon (3) of a balloon catheter (1). According to said method, the surface of the balloon (3) is at least partially wetted with a first solution of an active substance (8) and the section of the surface of the balloon (3) wetted with the first solution of an active substance (8) is then wetted with a second, saturated solution of the active substance (28). The invention further relates to a balloon (3) of a balloon catheter (1) the surface of which is at least partially coated with an active substance (11), the coating (11) being homogeneous and brittle in the entire coated region.

14 Claims, 3 Drawing Sheets

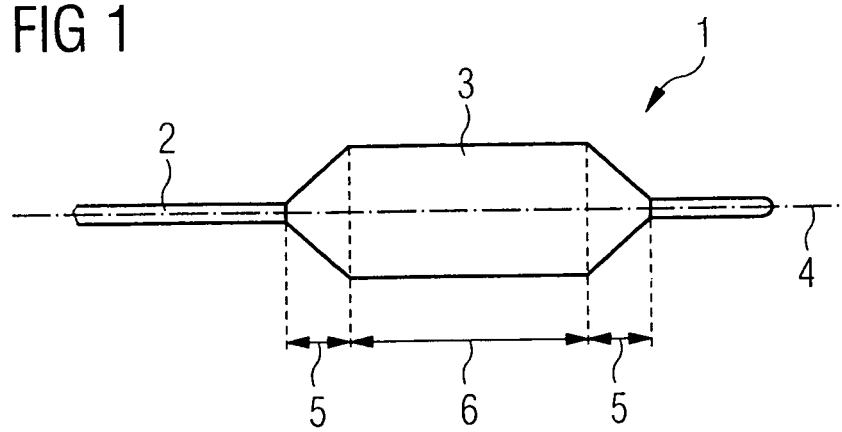
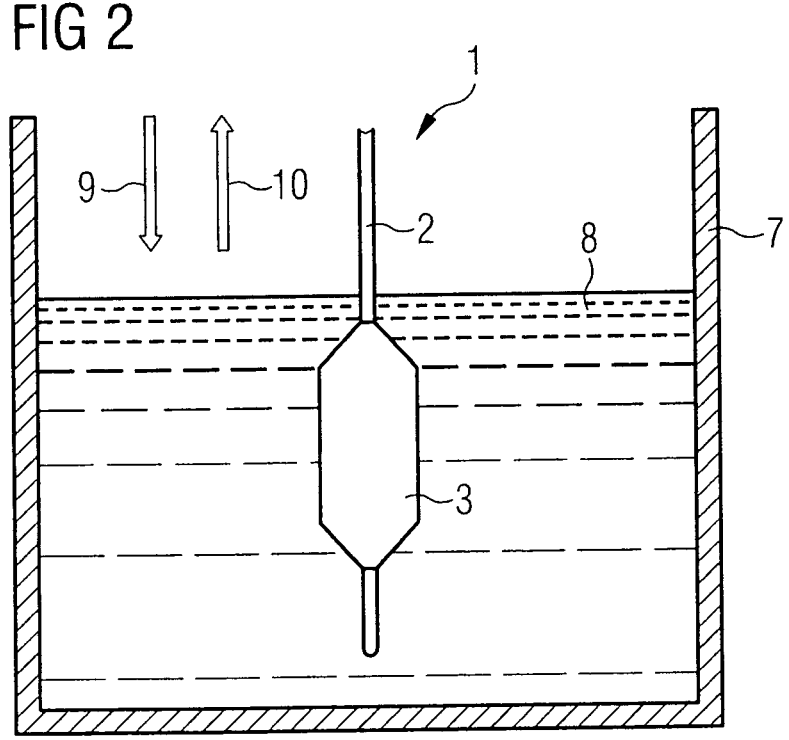

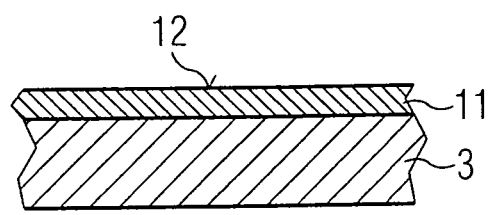
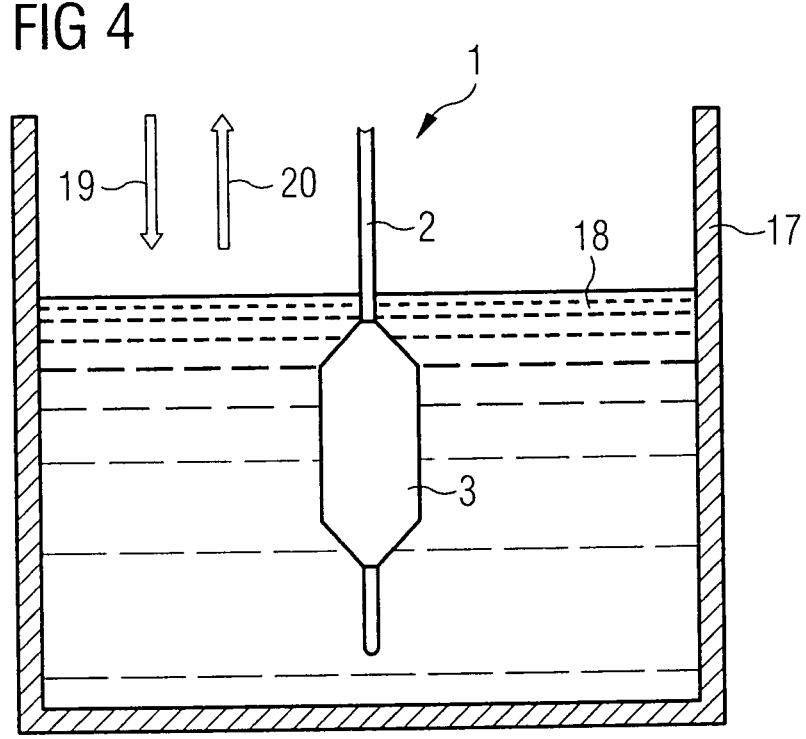

METHOD FOR PRODUCING A BIOACTIVE SURFACE ON THE BALLOON OF A BALLOON CATHETER

BACKGROUND OF THE INVENTION

The present invention concerns a method for producing a bioactive surface in the form of an active ingredient coating on the balloon of a balloon catheter. The invention concerns also a balloon of the balloon catheter and a balloon catheter.

The so-called "minimally invasive methods" gain increasingly in significance in medicine. In the context of radiology, interventional radiology is to be mentioned in this connection that has contributed significantly to the development of minimally invasive techniques and the devices and prostheses of suitable material required for this purpose. For example, today balloon catheters are inserted by cardiologists as well as radiologists in vessels in order to open them. These procedures may cause a thickening of the vessel wall with consecutive lumen constriction in the area of the expansion by cell proliferation.

By medication release from the surface of the balloon of the balloon catheter, this problem can be counteracted. Typically, an active ingredient that is dissolved in a solvent is applied to the surface of the balloon of the balloon catheter, wherein the solvent subsequently evaporates. The active ingredient is then located on the surface.

Possibilities for obtaining in comparison thereto an improved adhesion of the active ingredient on the surface are disclosed in the documents U.S. Pat. No. 5,102,402 and U.S. Pat. No. 6,129,705. The document U.S. Pat. No. 5,102,402 discloses a balloon catheter coated with medicaments. In this connection, in a first variant microcapsules filled with an active ingredient or medicament are enclosed by folds in the balloon surface and in this way mechanically held in their respective position. In a second variant the microcapsules are glued by means of a bonding agent to the balloon surface.

In the document U.S. Pat. No. 6,129,705 a balloon catheter is disclosed whose surface has a coating in which microcapsules that are filled with an active ingredient are completely embedded. However, filling the active ingredient in microcapsules and the subsequent attachment or embedding of the microcapsules on the balloon surface are comparatively complex and thus expensive methods.

In principle, it is desirable when the surface of the balloon of the balloon catheter has a homogenous and reproducible medicament loading and at the same time is distinguished by a uniform medicament release in the surrounding tissue in the body.

It is therefore a first object of the present invention to provide an advantageous method for producing a bioactive surface on the balloon of a balloon catheter. It is a second object of the invention to provide an advantageous balloon of a balloon catheter. A third object resides in that an advantageous balloon catheter is to be provided.

SUMMARY OF THE INVENTION

The first object is solved by a method in which the surface of the balloon at least partially is wetted with a first solution of an active ingredient, and the part of the surface of the balloon that is wetted with the first solution of an active ingredient is wetted with a second saturated solution of the active ingredient, the second object is solved by a balloon of a balloon catheter whose surface at least partially has a coating with an active ingredient, wherein the coating is embodied homogeneously and brittle within the entire coated area, and the third object is solved by a balloon catheter having a balloon with such a coating. The dependent claims contain further advantageous embodiments of the invention. The features are advantageous individually as well as in combination with each other.

In the method according to the invention for producing a bioactive surface on the balloon of a balloon catheter, the surface of the balloon is at least partially wetted with a first solution of an active ingredient. Subsequently, the part of the surface of the balloon that has been wetted with the first solution of an active ingredient is wetted with a second saturated solution of the active ingredient. In this connection, the surface of the balloon that has been wetted with the first solution of an active ingredient should dry slowly.

By wetting the surface of the balloon with the first solution of an active ingredient, on the surface a lacquer-like transparent active ingredient layer is produced that serves as a basis for a homogeneous and reproducible active ingredient loading. In this way, a large proportion, respectively, the predominant proportion of the entire active ingredient loading is applied. During wetting, the balloon material, in particular in case of the use of methylene chloride, can absorb solvent that is released again within a few hours under normal conditions.

By wetting with the second saturated solution of an active ingredient the entire coating becomes more brittle and optically less transparent i.e., more milky. The thus produced to surface has a chalk-like, in particular non-crystalline, consistency that enables an increased active ingredient removal by friction in comparison to a coating that is applied only by wetting the surface of the balloon with the first solution of the active ingredient. By means of the method according to the invention a higher active ingredient release from the balloon to the surrounding tissue in the body is achieved in comparison to a coating only by wetting of the surface of the balloon with the first solution of the active ingredient.

Basically, the entire balloon surface area as well as only a part of the balloon surface, for example, the area that upon expansion comes in contact with the tissue, can be coated with the method according to the invention. In particular, the balloon can have a cylindrical area and at least one conical area. In this case, for example, only the cylindrical area of the balloon can be coated according to the invention with the active ingredient or the cylindrical area of the balloon and one conical area.

Preferably, the second saturated solution may comprise ethanol or acetone. In ethanol or acetone the employed active ingredient is less soluble than in the solvent used in the context of the first solution. As a result of this, during wetting with the second saturated solution a portion of the active ingredient is dissolved out of the coating that has been produced in the context of the treatment with the first solution or this coating is attacked by the second solution and the surface becomes more porous or becomes partially brittle.

Moreover, the second saturated solution may comprise an azeotropic solvent.

As a first solution, in particular a saturated solution can be used, preferably a saturated solution of the active ingredient paclitaxel in methylene chloride. Other solvents, for example, chloroform or ethanol or solvent mixtures, can also be employed.

Advantageously, the surface of the balloon can be wetted with the first solution of an active ingredient by immersion of the balloon in the first solution. After immersion, the balloon can be removed from the first solution at a speed of up to 10 mm/s. It is even more beneficial when removal is performed at a speed of less than 5 mm/s, preferably at a speed of between 0.5 mm/s and 2 mm/s. By the slow removal a slower drying of the surface and thus formation of a lacquer-like active ingredient layer are achieved.

Moreover, the surface of the balloon before wetting with the first solution of an active ingredient can be cleaned and/or can be provided with a structure or profiling. The surface of the balloon can be, for example, mechanically, thermally or chemically structured or profiled. In particular, the surface can be structured or profiled by roughening. Advantageously, by enlarging the surface area of the balloon, depressions with a depth of 5-50 μm and a width of 5-50 μm are generated on the surface.

Moreover, the surface of the balloon, after wetting with the first solution of an active ingredient and before wetting with the second saturated solution, can be wetted with an additional, preferably non-saturated, solution of the active ingredient. In this way, the active ingredient loading is increased. The entire coating can be become more brittle by wetting with the additional solution of the active ingredient or can become partially brittle. Moreover, the entire coating can become optically less transparent, i.e., more milky. As a whole, wetting with the additional solution of the active ingredient leads to a higher active ingredient release by friction in comparison to the lacquer-like surface that is the result of wetting with the first solution.

When after wetting with the first solution of an active ingredient the step of wetting with the additional solution of an active ingredient is omitted, the active ingredient loading on the balloon surface is reduced as a result.

The additional solution, for example, can be a solution of paclitaxel in methylene chloride. Advantageously, the concentration of the solution should be less than that of the first solution, for example, 100 mg/ml. Other solvents, for example, chloroform or ethanol or solvent mixtures can also be used.

Moreover, the surface of the balloon can be wetted with the additional solution of the active ingredient by immersion of the balloon in the additional solution. The surface of the balloon can be immersed in or can be wetted with the additional solution of the active ingredient particularly maximally for 20 s, preferably between 0.5 and 10 s. The duration of wetting or of immersion can be made dependent on the active ingredient loading after wetting with the first solution. The higher the active ingredient loading after wetting with the first solution, the longer the surface of the balloon should be immersed in or wetted with the additional solution of the active ingredient. Preferably, the surface of the balloon can be wetted with the non-saturated solution of the active ingredient maximally 3 min. after wetting with the first solution of the active ingredient.

Moreover, wetting of the surface of the balloon with the second saturated solution of the active ingredient can be realized by immersion of the balloon in the second saturated solution. The surface of the balloon can be immersed in or can be wetted with the second saturated solution of the active ingredient in particular for maximally 20 s, advantageously between 0.5 s and 10 s. The duration of wetting or of immersion can be made depend on the active ingredient loading after wetting with the first solution or the active ingredient loading after wetting with the additional solution. The higher the active ingredient loading after wetting with the first solution or the additional solution, the longer the surface of the balloon should be immersed in or wetted with the second saturated solution of the active ingredient. Preferably, the surface of the balloon can be wetted with the second saturated solution of the active ingredient maximally 3 min. after wetting with the first solution of the active ingredient or maximally 3 min. after wetting with the additional solution.

The surface of the balloon can additionally be dried after wetting with the additional solution of the active ingredient and/or after wetting with the second saturated solution of the active ingredient. For example, the balloon may have a longitudinal axis and during drying can be rotated about its longitudinal axis. For a drying action as uniformly as possible, the longitudinal axis of the balloon can be brought in a horizontal position immediately after wetting with the additional solution and/or after wetting with the second saturated solution. The balloon can then be rotated in an air stream about its longitudinal axis.

The employed active ingredient can be in particular tretinoin and/or tretinoin derivatives and/or orphan receptor agonists and/or elafin derivatives and/or corticosteroids and/or steroid hormones and/or paclitaxel and/or paclitaxel derivatives and/or rapamune and/or tacrolimus and/or hydrophobic proteins and/or substances that modify cell proliferation or mixtures thereof. As steroid hormones methyl prednisolone, dexamethasone or estradiol can be used, for example.

In connection with the first solution and/or the second saturated solution and the non-saturated solution, for example, methylene chloride, chloroform, alcohol, in particular, ethanol, methanol or isopropanol, acetone, diethyl ether, liquid hydrocarbons, e.g. pentane, hexane, heptane, cyclohexane or octane, toluene, tetrahydrofurane (THF), or ethyl acetate can be used as solvents. The employed solvent may comprise in particular ethanol and water. The second saturated solution may contain acetic acid.

In the context of the second saturated solution, solvent mixtures, for example, a mixture that comprises ethanol and water, can be used. For example, the azeotropic solvent mixture can be comprised of 96% ethanol and 4% water, based on weight, respectively. This solvent mixture can contain moreover 0.1% acetic acid, based on volume. The acetic acid effects stabilization of the active ingredient, for example, paclitaxel.

The balloon of a balloon catheter according to the invention comprises a surface that has at least partially a coating with an active ingredient. The coating is embodied homogeneously and brittle within the entire coated area. The surface can have in particular a chalk-like or non-crystalline structure. Moreover, the surface of the balloon can be completely coated or only partly coated. In particular, the balloon can have a cylinder-shaped area and at least one conically shaped area. In this case, for example, only the cylindrically shaped area of the balloon or the cylindrically shaped area and one conical area can be coated according to the invention with an active ingredient. The balloon according to the invention can be produced in principle with the aid of the method according to the invention. It ensures a homogeneous and high medicament release to the surrounding tissue within the body.

The balloon catheter according to the invention comprises an afore described balloon according to the invention and has the same advantages as the balloon according to the invention.

Further features, properties and advantages of the present invention will be explained in the following with the aid of one embodiment with reference to the attached figures. The described features are advantageous individually as well as in combination with each other.

BRIEF DESCRIPTION OF THE DRAWINGS

FIG. 1 shows schematically a balloon catheter.
FIG. 2 shows schematically the immersion of the balloon catheter in the first solution of an active ingredient.

FIG. 3 shows schematically a section of a part of the balloon of the balloon catheter after immersion in the first solution.

FIG. 4 shows schematically immersion of the balloon catheter in the additional non-saturated solution.

DESCRIPTION OF PREFERRED EMBODIMENTS

Figure 5:
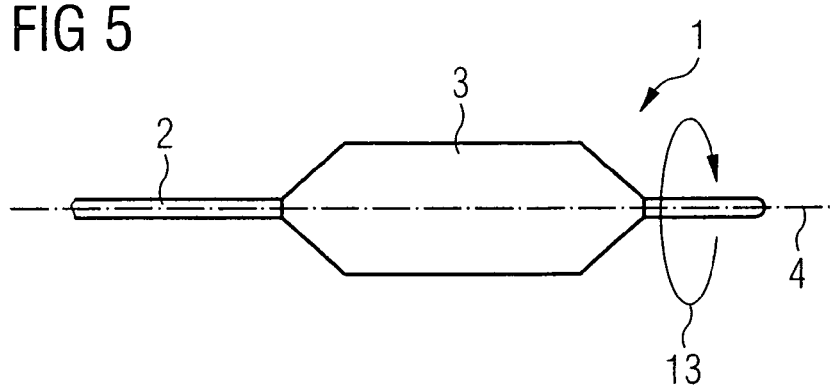
FIG. 5 shows schematically the rotation of the balloon catheter during the drying process after immersion in the additional non-saturated solution or in the second saturated solution.

In the following, an embodiment of the present invention will be explained in more detail with the aid of FIGS. 1 to 8. FIG. 1 shows schematically a balloon catheter 1. The balloon catheter 1 comprises a catheter probe 2 and a balloon 3. The balloon 3 surrounds a portion of the catheter probe 2. The longitudinal axis of the balloon catheter 1 is referenced by reference numeral 4. The balloon 3 comprises two conical areas 5 and a cylindrical area 6 arranged between the two conical areas 5.

In the context of the method according to the invention, the balloon 3 of the balloon catheter 1 is immersed first in a solution, preferably a saturated solution, of, for example, paclitaxel in methylene chloride. This is schematically illustrated in FIG. 2. FIG. 2 shows schematically a vessel 7 in which a first solution 8 is contained. The first solution 8 is, for example, a saturated solution of paditaxel in methylene chloride. Basically, also other solvents such as chloroform, ethanol or solvent mixtures are possible. The balloon 3 before immersion in the first solution 8 may first be cleaned or roughened and cleaned. The balloon 3 is preferably immersed completely in vertical direction in the first solution 8. Immersion is indicated by arrow 9 in FIG. 2. Subsequently, the balloon 3 is slowly pulled out again in vertical direction, preferably at a speed of approximately 1 mm/s, from the first solution 8. The removal is indicated in FIG. 2 by arrow 10. After removal 10, the balloon 3 is slowly dried.

By immersion in the first solution 8 and the slow removal and drying of the balloon 3, on the balloon 3 a transparent lacquer-like paditaxel layer is formed that is the basis for a homogeneous and reproducible total loading of the balloon 3 with the active ingredient paclitaxel. By immersion in the first solution 8 and slow removal and drying of the balloon 3, a large, respectively, a predominant portion of the active ingredient is applied to the balloon 3. The balloon material absorbs a significant amount of solvent during the immersion process which is released again within a few hours under normal conditions.

The coating on the surface of the balloon 3 that is produced by immersion in the first solution 8 is schematically indicated in FIG. 3. FIG. 3 shows a section of a part of the surface of the balloon 3. On the surface 3 of the balloon 3 an active ingredient layer 11 of paclitaxel is provided which, in turn, has a lacquer-like surface 12. The paclitaxel layer 11 as a whole is transparent.

In an optional step used in the present embodiment, the afore described coated balloon 3 of the balloon catheter 1 is immersed in an additional non-saturated solution 18 of paclitaxel in methylene chloride. The optional step is schematically illustrated in FIG. 4. FIG. 4 shows a vessel 17 in which the non-saturated solution 18 is contained. The non-saturated solution 18 has a concentration that is reduced in comparison to the first solution 8 employed in the first step. The non-saturated solution 18, for example, can be a solution of paditaxel in methylene chloride with a concentration of 100 mg/ml. Alternatively, other solvents, for example, chloroform, ethanol or solvent mixtures can be used. The immersion of the balloon 3 in the non-saturated solution 18 is indicated in FIG. 4 by arrow 19. The subsequent removal of the balloon 3 from the non-saturated solution 18 is indicated by arrow 20.

Preferably, the balloon 3 is immersed within up to 3 minutes after removal from the first solution 8 briefly, for example, for approximately 1 second, in the non-saturated solution 18. Alternatively, the balloon 3 may simply be wetted with the non-saturated solution 18. This can be done in particular by spraying.

For drying the balloon 3 as uniformly as possible after wetting or immersion in the non-saturated solution 18, the balloon catheter 1 or the balloon 3 is immediately transferred in a horizontal position with respect to its longitudinal axis 4 and is rotated in an air stream about its longitudinal axis 4. This is indicated schematically in FIG. 5. The rotation of the balloon catheter 1 about its longitudinal axis 4 is indicated by arrow 13.

Figure 6:
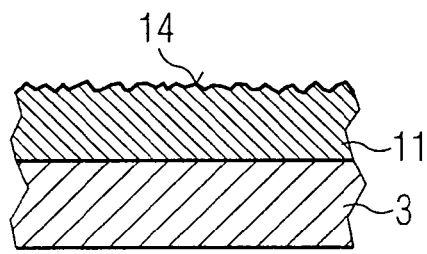
FIG. 6 shows schematically a section of a part of the surface of the balloon of the balloon catheter after immersion in the additional non-saturated solution.

By immersion of the balloon 3 in the non-saturated solution 18 or wetting of the balloon 3 with the non-saturated solution 18, the active ingredient loading of the balloon surface, in the present example the paclitaxel coating, is increased. Moreover, the entire coating becomes brittle or partially becomes brittle. Moreover, the entire coating becomes optically less transparent, i.e., more milky. As a whole, the described treatment with the non-saturated solution 18 leads to a higher active ingredient removal, i.e., a higher paclitaxel removal, from the balloon surface as a result of friction, FIG. 6 shows schematically a section of a part of the balloon surface 3 after treatment with the non-saturated solution 18. The active ingredient layer 11 that is located on the surface of the balloon 3, which in the present example is paclitaxel, has itself a brittle chalk-like surface 14.

Subsequent to the optional treatment which has been carried out in the present embodiment with the non-saturated solution 18, the balloon 3 is then immersed in a saturated solution of, for example, paclitaxel in an azeotropic mixture of, for example, ethanol and water with 0.1% acetic acid added. This is schematically indicated in FIG. 7.

Figure 7:
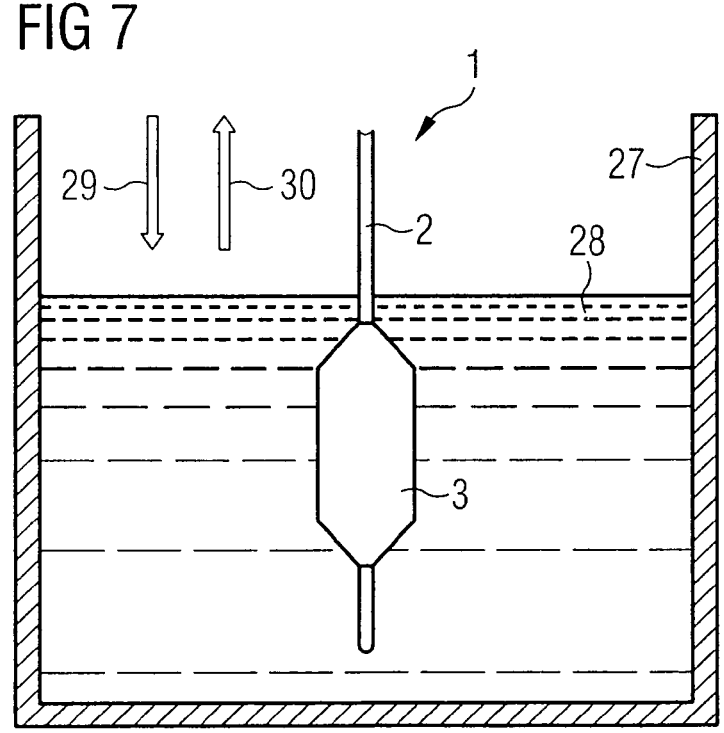
FIG. 7 shows schematically the immersion of the balloon catheter in the second saturated solution.

FIG. 7 shows a vessel 27 in which the second saturated solution of paclitaxel is contained in a mixture 28 of ethanol and water. For example, this can be an azeotropic mixture of 96% ethanol and 4% water, based on weight, respectively. The azeotropic mixture may contain additionally 0.1% acetic acid, based on volume. The acetic acid effects a stabilization of the employed active ingredient, in the present example of paclitaxel. The solubility of paclitaxel in the azeotropic mixture is less than in the saturated solution 8 and the non-saturated solution 18 of the solvents used in connection with the preceding steps.

Preferably, the balloon 3 that has been treated first with the saturated solution 8 and with the non-saturated solution 18, as described above, is immersed within up to 3 minutes after removal from the non-saturated solution 18 briefly in the second saturated solution in azeotropic mixture 28 or is wetted therewith. The immersion of the balloon 3 in the second saturated solution in azeotropic mixture 28 is identified in FIG. 3 by reference numeral 29. Removal of the balloon 3 from the second saturated solution in azeotropic mixture 28 is identified in FIG. 7 by reference numeral 30.

The balloon 3 is preferably immersed for approximately 1 second in the second saturated solution in azeotropic mixture 28. The duration of immersion depends on the layer thickness that has been achieved by the treatment with the first solution 8 and can last up to 20 seconds. After removal 30 of the balloon 3 from the second saturated solution in the azeotropic mixture 28 the balloon 3 is moved immediately into a horizontal position for drying as uniformly as possible and is rotated in an air stream about its longitudinal axis 4, as already described in connection with FIG. 5 above.

Figure 8:
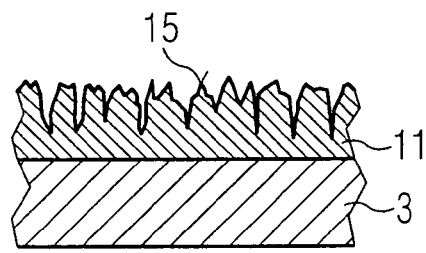
FIG. 8 shows schematically a section of a part of the surface of the balloon of the balloon catheter after immersion in the second saturated solution.

As a result of the described treatment of the balloon 3 with the second saturated solution of paclitaxel in the azeotropic mixture 28, the entire coating 11 becomes more brittle and optically less transparent, i.e. more milky. This is indicated schematically in FIG. 8. FIG. 8 shows schematically a section of a part of the surface of the balloon 3 after the treatment with the second saturated solution in the azeotropic mixture 28. On the surface of the balloon 3 there is an active ingredient layer of paclitaxel that has itself a brittle chalk-like surface 15. In comparison to the surface 14 of the paclitaxel layer 11 shown in FIG. 6, the surface 15 that is produced as a result of the treatment with the second saturated solution in azeotropic mixture 28 is more brittle and has a higher paclitaxel removal by friction.

In principle, the treatment explained in connection with FIGS. 4 to 6 with the additional non-saturated solution 18, i.e., immersion of the balloon 3 in the solution 18 or wetting of the surface of the balloon 3 with the non-saturated solution 18, can be omitted. In this case, the balloon 3 within maximally 3 minutes after complete removal from the first solution 8 is immersed in the second saturated solution in the azeotropic mixture 28 or is wetted therewith. When the treatment with the non-saturated solution 18 is omitted, the active ingredient loading on the surface of the balloon 3 as a whole is reduced. Also, in this case the brittleness of the generated surface of the active ingredient coating 11 is greater.

In principle, the surface of the balloon 3 can be completely or only partly coated. In is particular, only the cylinder-shaped area 6 of the balloon 3 can be coated with the active ingredient in accordance with the invention because mainly the cylinder-shaped area 6 of the balloon 3 will come in contact with the surrounding tissue in the body to be treated.

What is claimed is:

1. A method for coating a surface of a balloon of a balloon catheter with an active ingredient, comprising the steps of:
   a) producing an active ingredient layer, consisting of an active ingredient, as a lacquer-like coating across the outermost surface of the balloon by
      aa) applying the active ingredient to the outermost surface of the balloon by wetting the surface of the balloon with a first solution comprised of the active ingredient and a first solvent with partial absorption of the first solvent by the balloon through the surface of the balloon;
      ab) drying the surface of the balloon wetted with the first solution;
   b) converting the active ingredient layer of step a) to a chalk-like coating with improved active ingredient release from the balloon by applying a second solution comprised of a second solvent and the active ingredient.

2. The method according to claim 1, wherein in step b) the surface of the balloon is wetted with the second solution, wherein the second solution is a saturated solution of the active ingredient.

3. The method according to claim 2, wherein the second solvent comprises ethanol or acetone.

4. The method according to claim 2, wherein the second solvent comprises an azeotropic solvent.

5. The method according to claim 1, wherein in the step aa) the balloon is immersed in the first solution and removed at a speed of up to 10 mm/s from the first solution.

6. The method according to claim 1, further comprising the step of wetting the surface of the balloon with an additional solution of the active ingredient after step a) and before step b).

7. The method according to claim 6, wherein wetting of the surface of the balloon with the additional solution of the active ingredient is realized by immersion of the balloon in the additional solution.

8. The method according to claim 7, wherein the balloon is immersed maximally for 20 s in the additional solution.

9. The method according to claim 6, wherein the step of wetting the surface of the balloon with an additional solution is done maximally 3 min. after wetting with the first solution.

10. The method according to claim 6, further comprising the step of drying the surface of the balloon after the step of wetting with the additional solution.

11. The method according to claim 1, wherein the active ingredient is selected from the group consisting of tretinoin, tretinoin derivatives, orphan receptor agonists, elafin derivatives, corticosteroids, steroid hormones, paclitaxel, paclitaxel derivatives, rapamune, tacrolimus, hydrophobic proteins, and substances that modify cell proliferation.

12. The method according to claim 1, wherein the first solvent is selected from the group consisting of methylene chloride, chloroform, alcohol, acetone, diethyl ether, liquid hydrocarbons, toluene, tetrahydrofurane (THF), and ethyl acetate.

13. The method according to claim 1, wherein the second solvent comprises ethanol and water.

14. The method according to claim 1, wherein the second solution is a saturated solution and comprises acetic acid.

* * * * *